(12) United States Patent
Weiser et al.

(10) Patent No.: US 11,730,853 B2
(45) Date of Patent: Aug. 22, 2023

(54) METHOD FOR PRODUCING AN ADHESIVE-FREE WOUND CONTACT COMPOSITE MATERIAL

(71) Applicant: Covestro Deutschland AG, Leverkusen (DE)

(72) Inventors: Marc-Stephan Weiser, Kürten-Dürscheid (DE); Sascha Plug, Leverkusen (DE); Sebastian Dörr, Düsseldorf (DE)

(73) Assignee: Covestro Intellectual Property GmbH & Co. KG, Leverkusen (DE)

( * ) Notice: Subject to any disclaimer, the term of this patent is extended or adjusted under 35 U.S.C. 154(b) by 820 days.

(21) Appl. No.: 16/485,890

(22) PCT Filed: Feb. 13, 2018

(86) PCT No.: PCT/EP2018/053584
§ 371 (c)(1),
(2) Date: Aug. 14, 2019

(87) PCT Pub. No.: WO2018/149835
PCT Pub. Date: Aug. 23, 2018

(65) Prior Publication Data
US 2020/0054781 A1 Feb. 20, 2020

(30) Foreign Application Priority Data
Feb. 16, 2017 (EP) ..................... 17156493

(51) Int. Cl.
*A61F 13/00* (2006.01)
*B32B 27/06* (2006.01)
(Continued)

(52) U.S. Cl.
CPC ........ *A61L 15/26* (2013.01); *A61F 13/00017* (2013.01); *A61F 13/00029* (2013.01);
(Continued)

(58) Field of Classification Search
CPC ................. A61L 15/26; A61L 2420/02; A61F 13/00017; A61F 13/00029;
(Continued)

(56) References Cited

U.S. PATENT DOCUMENTS 4,541,426 A * 9/1985 Webster ................. B32B 27/08
602/42
9,364,577 B2 6/2016 Niesten et al.
(Continued)

FOREIGN PATENT DOCUMENTS

| EP | 0097517 A1 | 1/1984 | |
| WO | WO-2008156285 A1 | 12/2008 | |
| WO | WO-2012150224 A1 * | 11/2012 | ......... A61F 13/0206 |

OTHER PUBLICATIONS

International Search Report for PCT/EP2018/053584 dated Apr. 24, 2018.
(Continued)

*Primary Examiner* — Kim M Lewis
(74) *Attorney, Agent, or Firm* — The Webb Law Firm

(57) ABSTRACT

The invention relates to a process for producing a composite material for wound dressings, comprising the following steps: (I) providing a first film, having a first film surface and a second film surface running virtually parallel to the first film surface: (II) mixing an NCO-terminated polyurethane prepolymer with at least water to give a polyurethane prepolymer/water mixture, (III) applying the polyurethane prepolymer/water mixture to at least one part of the first film surface to form a layer, the layer having a first layer surface which is in contact with the first film via at least one part of the first film surface, and having a second layer surface which runs virtually parallel to the first layer surface; (IV) covering at least one part of the second layer surface with a further film, wherein the bond strength between the first film and the layer and also between the layer and the further film
(Continued)

Figure 1:
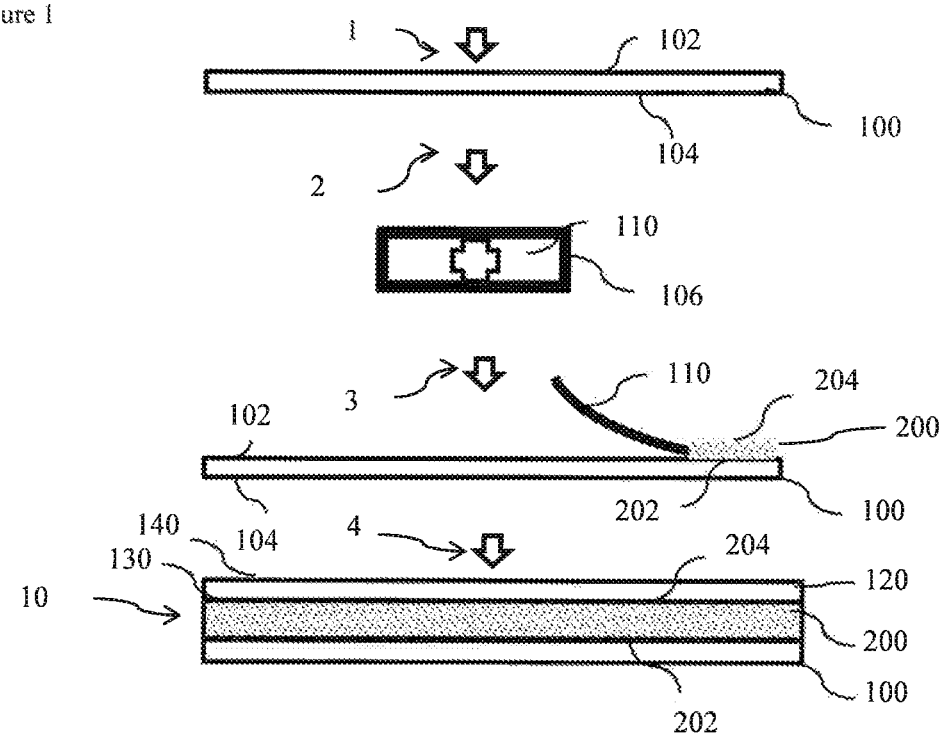

is greater in each case than the tensile strain at break of the layer. The invention further relates to a composite material produced by the process of the invention and also to a wound dressing comprising such a composite material and also to the use thereof in a wound dressing for improving the absorption of wound secretion and the distribution of secretion in the wound dressing.

12 Claims, 1 Drawing Sheet

(51) Int. Cl.
    *B32B 27/40* (2006.01)
    *A61L 15/26* (2006.01)
    *B32B 3/26* (2006.01)
    *B32B 5/20* (2006.01)
    *B05D 1/26* (2006.01)
    *A61L 15/42* (2006.01)
    *A61F 13/02* (2006.01)
    *C08J 7/04* (2020.01)

(52) U.S. Cl.
    CPC .... *A61F 13/00042* (2013.01); *A61F 13/0286* (2013.01); *A61L 15/425* (2013.01); *B05D 1/26* (2013.01); *B32B 3/266* (2013.01); *B32B 5/20* (2013.01); *B32B 27/065* (2013.01); *B32B 27/40* (2013.01); *C08J 7/04* (2013.01); *A61L 2420/02* (2013.01); *B32B 2266/0278* (2013.01); *B32B 2307/72* (2013.01); *B32B 2307/724* (2013.01); *B32B 2307/726* (2013.01); *B32B 2535/00* (2013.01); *C08J 2375/04* (2013.01); *C08J 2475/04* (2013.01)

(58) Field of Classification Search
    CPC ..... A61F 13/00042; B32B 3/266; B32B 5/20; B32B 27/065; B32B 27/40
    USPC ........................................................ 427/491
    See application file for complete search history.

(56) References Cited

U.S. PATENT DOCUMENTS

2009/0093179 A1* 4/2009 Kong ................. B32B 7/12
  428/354
2016/0046105 A1* 2/2016 Markowski ............ B32B 7/12
  156/60

OTHER PUBLICATIONS

Written Opinion of the International Searching Authority for PCT/EP2018/053584 dated Apr. 24, 2018.

* cited by examiner

METHOD FOR PRODUCING AN ADHESIVE-FREE WOUND CONTACT COMPOSITE MATERIAL

CROSS-REFERENCE TO RELATED APPLICATIONS

This application is a national stage application (under 35 U.S.C. § 371) of PCT/EP2018/053584, filed Feb. 13, 2018, which claims benefit of European Application No. 171564913, tiled Feb. 16, 2017, both of which are incorporated herein by reference in their entirety.

The present invention relates to a process for producing a composite material for wound dressings, comprising the steps of (I) providing a first film, (II) mixing an NCO-terminated polyurethane prepolymer with at least water to give a polyurethane prepolymer/water mixture, (III) applying the polyurethane prepolymer/water mixture to at least one part of the first film surface to form a layer, (IV) covering at least one part of the second layer surface with a further film. The invention further relates to a composite material comprising the first film, the layer and the further film, the composite material having no additional material between the layer and the films, and also to a wound dressing comprising the composite material of the invention, and to the use of the composite material of the invention for producing wound dressings, for the purpose of improving the absorption of wound secretion and the distribution of secretion in the wound dressing.

Described in the prior art are composite materials for wound dressings that have an adhesive, in the form of a layer of adhesive, for example, between the films used and the foam layer that serves for accommodation of fluid in the wound dressing, where the material of the adhesive differs from the material of the films and/or of the layer. This adhesive is needed in order to allow sufficient adhesion of the layer to the films. In order to apply this adhesive between the films and the layer, separate operations are required in the production of the composite material. This results in additional use of time, consumption of material, costs, and increased complexity to the construction of the composite material.

It is an object of the present invention to improve at least a part of the disadvantages of the prior art at least partly.

It is a further object of the invention to provide a process for producing a composite material that as far as possible is cost-saving and time-saving and has as few process steps as possible.

It is an object of the present invention, moreover, to provide a composite material for wound dressings that can be produced as far as possible with cost savings, time savings, and with minimal complexity of construction.

A further object of the present invention is to provide a composite material for wound dressings that permits improved absorption of wound secretion relative to conventional composite materials and/or permits improved distribution of secretion in the composite material and/or in the wound dressing comprising the composite material.

At least one of the objects is achieved by a process far producing a composite material according to the subject matter of Claim 1, Particular embodiments are described in the dependent claims. Furthermore, at least part of the objects is achieved by a composite material and/or by a wound material comprising the composite material produced by the process of the invention. In turn, a part of the objects is solved by the use of the composite material of the invention for improving the absorption of wound secretion and the distribution of secretion in the wound dressing.

A first subject of the invention is a process for producing a composite material for wound dressings, comprising the following steps:
(I) providing a first film, having a first film surface and a second film surface running virtually parallel to the first film surface;
(II) mixing an NCO-terminated polyurethane prepolymer with at least water to give a polyurethane prepolymer/water mixture,
(III) applying the polyurethane prepolymer/water mixture to at least one part of the first film surface to form a layer, the layer having a first layer surface which is in contact with the first film via at least one part of the first film surface, and having a second layer surface which runs virtually parallel to the first layer surface;
(IV) covering at least one part of the second layer surface with at least one further film surface of a further film to give the composite material,
wherein the bond strength between the first film and the layer and also between the layer and the further film is greater in each case than the tensile strain at break of the layer, so that the layer tears within itself when an attempt is made to remove a film from the layer.

In accordance with the invention, the bond strength is higher than the tensile stress at break of the layer when the layer cannot be parted without residue from the first or the further film. This means that when the first or the further film is separated from the layer, the layer suffers cohesive fracture, and not adhesive fracture, in which case the bond strength would be lower than the tensile strain at break of the layer. In contrast to an adhesive fracture, which would represent a separation of the composite at the adhesion surface between the respective film and the layer and would allow the films to be separated without residue from the layer, the cohesive fracture occurs in the interior of the layer and leaves behind residues of the layer material on the particular film which is to be removed.

In the process of the invention, there is preferably no further material applied between the steps (I) and (IV) to the first film, the layer or the further film in such a way that there would be further material between the layer and the films. The composite material as produced in the process of the invention preferably comprises no thriller adhesive-containing materials between the materials provided and processed in step (I) to (IV). The materials for the first film and also for the further film are preferably selected such that the bond strength between the films and the layer is greater than the tensile stress at break of the layer. The bond strength is preferably in a range from 10 to 500%, or preferably in a range from 20 to 450%, or preferably in a range from 50 to 400%, or preferably in a range from 100 to 300%, greater than the tensile stress at break of the layer.

Following application and covering in steps (III) and (IV), the layer formed preferably has a sufficient bond strength between the first film and the layer, and also between the layer and the further film, to keep the composite together even under loading.

For the purposes of the invention, a sufficient bond strength, or a bond strength between the films and the layer that is greater than the tensile stress at break of the layer, means that when an attempt is made to remove at least one of the two films, such as the first film or the further film, from the layer, a visible or perceptible residue of layer material remains or is left at least on one part of the first film surface of the first film or of the further film surface of the further film. Consequently, when an attempt is made to separate at least one of the films from the layer, there is cohesive fracture in the layer. Residue-free removal of the films from the layer is not possible when an attempt is made to separate at least one of the films from the layer. Irrespective of the force needed to pull the composite apart, the bond strength is always greater than the tensile stress at break of the foam. The tensile stress at break is the maximum force, in the form of mechanical loading, for example, which is withstood by the material before it breaks. It is reported as force per cross-sectional area. The tensile stress at break of the layer, measured via DIN EN ISO 527-2, is preferably at least 0.04 MPa.

The bond strength of the layer to the films is preferably sufficient to hold the composite together for application in a wound material sufficiently for customary use thereof in the medical environment or in the wound management environment. The holding-together of the composite has the effect that the picking apart or pulling apart of the composite material into its original minimum constituents, such as the first film, the layer and the further film, is not possible without destruction of the composite material, more particularly of the layer material. A consequence of this is that the minimum constituents cannot be recovered in the form as originally used without residues of the layer material on at least one of the films. For instance, an attempt to remove the first film or the further film from the layer would result in the first or further film having parts of the layer on its surface. Furthermore, the layer, after production of the composite by the process of the invention, preferably has no bond strength relative to other materials which are later brought into contact with it. The tensile stress at break of the first film and/or of the further film is preferably greater than the tensile stress at break of the layer. The tensile stress at break of the first film and/or of the further film is preferably greater than the bond strength between the respective film and the layer.

Even if the composite material itself is preferably of adhesive-free construction within the composite, it is possible for a further material, such as a third film, to be adhered to the composite via a layer of adhesive on the outside of the composite, in other words on that surface of the first film or further film that is disposed remote from the layer in each case.

The first film may be provided in any way which the skilled person would select for the purpose. It is preferably provided in step (I) by means of a roll-to-roll operation. It is also conceivable, however, for cut-to-size films to be provided on a preferably flat surface which is at least as large as the first film. The first film and/or the further film preferably have apertures, preferably in the form of holes.

The mixing in step (II) may take place in any way which the skilled person would select for the purpose. The mixing in step (II) takes place preferably by means of a two-component low-pressure mixing assembly with dynamic, static-dynamic or static stirrer, or with a stirrer selected from the group consisting of a magnetic stirrer, a laboratory dissolver, a Dispermat, or another apparatus known to the skilled person and suitable for mixing liquids. The polyurethane prepolymer/water mixture is prepared preferably in an amount of 0.11 to 10,000 l in step (II). The polyurethane prepolymer water mixture is prepared preferably by the combining of at least one NCO-terminated polyurethane prepolymer with water. The NCO-terminated polyurethane prepolymer and water react to form urea groups and with elimination of $CO_2$, thus giving a polyurethane foam. The prepolymer is customarily in a liquid form.

The NCO-terminated polyurethane prepolymer is preferably obtainable from the reaction of a reaction mixture comprising a polyisocyanate and polyol. The polyisocyanate preferably has an NCO functionality in a range from >1.5 to 6, or preferably from 1.8 to 5, or preferably from 2 to 4, more particularly of 2. Suitable polyisocyanates are aliphatic, aromatic araliphatic or cycloaliphatic polyisocyanates. Examples of such suitable polyisocyanates are butylene 1,4-diisocyanate, hexamethylene 1,6-diisocyanate (HDI), isophorone diisocyanate (IPDI), 2,2,4—and/or 2,4,4-trimethylhexamethylene diisocyanate, the isomeric bis(4,4'-isocyanatocyclohexyl)methanes or mixtures thereof with any desired isomer content, cyclohexylene 1,4-diisocyanate, 4-isocyanatomethyloctane 1,8-diisocyanate (nonane triisocyanate), phenylene 1,4-diisocyanate, tolylene 2,4—and/or 2,6-diisocyanate, naphthylene 1,5-diisocyanate, diphenylmethane 2,2'- and/or 2,4'- and/or 4,4'-diisocyanate, 1,3—and/or 1,4-bis(2-isoeyanatoprop-2-yl)benzene (TMXDI), 1,3-bis(isocyanatomethyl/benzene (XDI) and also alkyl 2,6-diisocyanatohexanoates (lysine diisocyanates) with C1-C8 alkyl groups.

The polyisocyanate is preferably an aliphatic polyisocyanate. Preferred aliphatic diisocyanates are hexamethylene diisocyanate and isophorone diisocyanate and also mixtures thereof.

The polyol preferably has an OH functionality of >1.5 to 6 or preferably from 1.8 to 5, or preferably from 2 to 4, more particularly of 3. The polyol is preferably selected from the group consisting of a polyether polyol, a polycarbonate polyol, a polyether polycarbonate polyol, a polyester polyol or a mixture of at least two thereof. Preferably the polyol is a polyether polyol. The polyol preferably comprises a polyol containing polyoxyethylene groups. With regard to the polyols, preference is given to copolymers of ethylene oxide and propylene oxide having an ethylene oxide content, based on the total amount of the oxyalkylene groups present, of 60 to 85 mol %.

Alternatively, either the water or an aqueous mixture can be added to the prepolymer or a prepolymer mixture, or, conversely, the prepolymer or the prepolymer mixture can be added to water or the aqueous mixture. It is likewise possible for two streams (prepolymer/prepolymer mixture and water/aqueous mixture) to be brought together in a mixing element.

Preferably, moreover, step (II) is carried out in the presence of a base. The base preferably has a $pK_b$ of ≥6, more preferably ≥7. Particularly preferred is a $CO_2$-releasing base such as hydrogencarbonate.

The applying in step (III) may take place in any way which a skilled person would select for the purpose. The applying in step (III) is preferably selected from the group consisting of pouring, coating, in which case preferably any kind of coating is suitable, contactless printing, screen printing, brush application, spraying, or a combination of at least two thereof. Applying takes place preferably by means of an applicator in a coating process, preferably a roll coating process or a knifecoating process. The knife applicator is preferably selected from a metal knife, a wooden knife, a plastic knife, a rubber knife or a combination of at least two thereof. Instead of a knife, it is also possible for one or more rollers or rolls to be used as applicators. The gap between the applicator and the film to be coated, such as the knife gap or the gap between roller and first film, preferably has a thickness in a range from 100 μm to 1 cm, or preferably in a range from 250 μm to 5 mm. The applicator, for example the knife or the roll, is moved preferably at a speed in a range from 0.1 to 30 m/min, or preferably in a range from 1 to 20 m/min, or preferably in a range from 2 to 10 m/min, or, when using a fixed applicator, such as knife or roll, the web is moved beneath the knife or the roll with a speed within the speed ranges specified above. As a result of the elimination of $CO_2$ after mixing the polyurethane prepolymer/water mixture in step (II), the layer is formed from the applied mixture in step (III), preferably in the form of an open-cell foam. The polyurethane prepolymer/water mixture preferably has a density in a range from 900 g/l to 1200 g/l, or preferably in a range from 950 g/l to 1150 g/l, or preferably in a range from 1000 to 1100 g/l. The layer in the form of a foam preferably has an average pore size in a range from 100 to 700 μm, preferably in a range from 120 to 400 μm or preferably in a range from 150 to 250 μm. The resulting layer in the form of the foam preferably has a lower density than the polyurethane prepolymer/water mixture on preparation thereof. The layer preferably has a density which is in a range from 3 to 10 times, or preferably in a range from 3.5 to 9.5.times, or preferably in a range from 4 to 9 times greater than the density of the polyurethane prepolymer/water mixture. The layer preferably has a density in a range from 90 g/l to 350 g/l, or preferably in a range from 100 g/l to 280 g/l, or preferably in a range from 110 to 180 g/l.

The covering of at least one part of the second layer surface of the layer with a further film in step (IV) takes place preferably by means of a process selected from the group consisting of depositing, laminating, or a combination thereof. The further film is preferably deposited from roll to roll onto the layer which is formed in step (III), this layer preferably still being liquid.

The first film may comprise any material which the skilled person would use for the purpose. The first film preferably comprises a material suitable for developing a bond strength with respect to the layer that is greater than the elongation at break of the layer. The first film preferably comprises a material which is capable of developing a bond strength between the layer and the first film of more than 0.5 N/20 mm, or preferably more than 1 N/20 mm, or preferably more than 2 N/20 mm, or preferably in a range from 0.5 N/20 mm to 30 N/20 mm, or preferably in a range from 1 N/20 mm to 25 N/20 mm, or preferably in a range from 2 N/20 mm to 15 N/20 mm. The first film preferably comprises a material selected from the group consisting of a polymer, a fabric, a metal or a combination of at least two thereof. The first film preferably comprises a polymer, and with particular preference the first film consists of a polymer. The material of the first film is preferably selected from the group consisting of a polypropylene, a polyethylene, a polyimide, a polyamide, a polyacrylamide, a polyethylene terephthalate, a polycarbonate, a polymethyl methacrylate, a polysulphone, a polyhydroxyethyl methacrylate, a polyurethane, preferably a thermoplastic polyurethane, a cellulose triacetate, a polyethylene copolymer, a rubber or a mixture or combination of at least two thereof.

The first film preferably has a total surface area in a range from 1 $cm^2$ to 1000 $m^2$, or preferably in a range from 10 $cm^2$ to 500 $m^2$, or preferably in a range from 50 $cm^2$ to 100 $m^2$, with possible apertures being included for the calculation or measurement of the total surface area of the first film. The apertures in the film preferably occupy an area in a range from 5 to 50%, or preferably in a range from 10 to 45%, or preferably from 15 to 40% of the total surface area of the first film.

The materials comprised by the fill further film are preferably selected from the same materials as specified for the first film. The proportions of the materials for the further film are preferably the same as specified for the first film.

Furthermore, the total area of the further film is preferably within the same range as specified for the first film.

In one preferred embodiment of the process of the invention, at least steps (III) and (IV) taken together, preferably steps (II) to (IV) taken together, take place within a period of less than 120 seconds, preferably of less than 90 seconds, or preferably of less than 60 seconds or preferably of less than 40 seconds. The time elapsed in between the stirred preparation of the polyurethane/water mixture in step (II) and the application of this mixture to the first film in step (III) is preferably not more than 120 seconds, preferably not more than 90 seconds, or preferably not more than 60 seconds or preferably not more than 40 seconds. The time between the stirred preparation of the polyurethane/water mixture in step (II) and the application of the further film in step (IV) to the polyurethane/water mixture applied to the first film in step (III) is preferably not more than 120 seconds, preferably not more than 90 seconds, or preferably not more than 60 seconds or preferably not more than 40 seconds.

In one preferred embodiment of the process of the invention, the composite material has no further material between the first film and the layer and also between the further film and the layer. As already mentioned, however, the composite material may have further materials, such as adhesives, for example, on its outside, in other words on a surface of the first film or of the further film that is not in connection with the layer.

The polyurethane prepolymer/water mixture is preferably applied in step (III), preferably in the form of a wet layer, with a wet layer thickness, which is determined by the knife gap, in a range from 50 to 5000 μm, preferably in a range from 100 to 3000 μm, or preferably in a range from 300 to 2000 μm. The wet layer is covered with the further film preferably within from 1 to 90 seconds, or preferably from 2 to 80 seconds, or preferably within from 5 to 60 seconds. The wet layer cures preferably within from 1 to 10 minutes, preferably within from 2 to 8 minutes, or preferably within from 3 to 6 minutes, to an extent of at least 50%, or preferably at least 60%, or preferably at least 70%, based on the total amount of liquid which escapes during the entire curing process.

In one preferred embodiment of the process of the invention, the layer has a thickness after curing which is 1.5 to 30 times, or preferably 2 to 10 times, or preferably 2.5 to 5 times greater than the thickness on application of the polyurethane prepolymer/water mixture in step (III). The thickness of the layer after curing is preferably in a range from 70 μm to 10 cm, or preferably in a range from 100 μm to 5 cm, or preferably in a range from 200 μm to 10 cm, or preferably in a range from 500 μm to 1 cm.

In one preferred embodiment of the process of the invention, the NCO-terminated polyurethane prepolymer has a weight fraction of low molecular mass, aliphatic diisocyanates having a molar mass of ≥140 to ≤278 g/mol of ≤1.0 wt %, based on the prepolymer, and is obtainable as component A) by reaction of
  A1) low molecular mass, aliphatic diisocyanates with a molar mass of ≥140 to ≤278 g/mol with
  A2) di- to hexa-functional polyalkylene oxides with an OH number of ≥22.5 to ≤112 mg KOH/g and an ethylene oxide fraction of ≥50 to ≤100 mol %, based on the total amount of the oxyalkylene groups present.

The NCO-terminated polyurethane prepolymer is preferably obtainable from the reaction of a reaction mixture comprising a low molecular mass, aliphatic diisocyanate and a polyol containing polyoxyethylene groups. With regard to the low molecular mass, aliphatic diisocyanates, preference is given to hexamethylene diisocyanate and isophorone diisocyanate and also mixtures thereof. With regard to the polyols, preference is given to copolymers of ethylene oxide and propylene oxide having an ethylene oxide content, based on the total amount of the oxyalkylene groups present, of 60 to 85 mol %.

The NCO-terminated polyurethane prepolymer preferably further comprises:

H1) one or more low molecular mass, aliphatic diisocyanates having a molar mass of ≥140 to ≤278 g/mol, preferably ≥168 to ≤258 g/mol, and/or polyisocyanates preparable therefrom and having an isocyanate functionality of ≥2 to ≤6;

and/or

H2) one or more monofunctional polyalkylene oxides having an OH number of ≥10 to ≤250 and an ethylene oxide fraction of ≥50 to ≤100 mol %, based on the total amount of the oxyalkylene groups present;

and/or a hydrophilic isocyanate component which is obtainable by the reaction of components identified under H1) with components identified under H2).

The NCO-terminated polyurethane prepolymer preferably comprises:

A) isocyanate-functional prepolymers having a weight fraction of low molecular mass, aliphatic diisocyanates with a molar mass of ≥140 to ≤278 g/mol, preferably ≥168 to ≤258 g/mol, of ≤1.0 wt %, based on the prepolymer, obtainable by reaction of A1) low molecular mass, aliphatic diisocyanates with a molar mass of ≥140 to ≤278 g/mol, preferably ≥168 to ≤258 g/mol with A2) di- to hexa-functional polyalkylene oxides with an OH number of ≥22.5 to ≤112 mg KOH/g and an ethylene oxide fraction of ≥50 to ≤100 mol %, based on the total amount of the oxyalkylene groups present, B) optionally heterocyclic, 4-ring or 6-ring oligomers of low molecular mass, aliphatic diisocyanates having a molar mass of ≥140 to ≤278 g/mol, preferably ≥168 to ≤258 g/mol, D) optionally catalysts, E) optionally alkali metal salts of weak inorganic acids, F) optionally surfactants, G) optionally mono- or polyhydric alcohols, H) the following components;

H1) one or more low molecular mass, aliphatic diisocyanates having a molar mass of ≥140 to ≤278 g/mol, preferably ≥168 to ≤258 g/mol, and/or polyisocyanates prepayable therefrom and having an isocyanate functionality of ≥2 to ≤6;

and/or

H2) one or more monofunctional polyalkylene oxides having an OH number of ≥10 to ≤250 and an ethylene oxide fraction of ≥50 to ≤100 mol %, based on the total amount or the oxyalkylene groups present;

and/or a hydrophilic isocyanate component which is obtainable by the reaction of components identified under H1) with components identified under H2).

The prepolymers A) used preferably have a residual monomer content (monomers correspond to low molecular mass, aliphatic diisocyanates) of below 0.5 wt %, based on the prepolymer. This content may be achieved by correspondingly selected quantities of the diisocyanates A1) and of the polyalkylene oxides A2) used. Preference, however, is given to the use of the diisocyanate A1) in excess and with subsequent, preferably distillative, removal of unreacted monomers.

In the preparation of the isocyanate-functional prepolymers A), the ratio of the polyalkylene oxides A2) to the low molecular mass, aliphatic diisocyanates A1) is typically set such that for each mole of OH groups of the polyalkylene oxides A2) there are 2 to 20 mol, preferably 2 to 10 mol and more preferably 5 to 10 mol of NCO groups of the low molecular mass, aliphatic diisocyanate A1).

The hydrophilic polyisocyanates identified under H) are typically prepared by reaction of 1 mol of OH groups of the monofunctional polyalkylene oxide component H2) with 1.25 to 15 mol, preferably 2 to 10 mol and more preferably 2 to 6 mol of NCO groups of a polyisocyanate having an isocyanate functionality of 2 to 6, based on aliphatic diisocyanates. Exemplary of such polyisocyanates H1) are biuret structures, isocyanurates and/or uretdiones based on aliphatic diisocyanates. In this case the polyisocyanate H1) and the polyalkylene oxide H2) are linked to one another preferably via a urethane group and/or a urea group, with linkage via urethane groups being particularly preferred.

The NCO content of the isocyanate-functional prepolymers A) is preferably 1.5 to 4.5 wt %, more preferably 1.5 to 3.5 wt % and very preferably 1.5 to 3.0 wt %.

Examples of low molecular mass, aliphatic diisocyanates of component A1) are hexamethylene diisocyanate (HDI), isophorone diisocyanate (IPDI), butylene diisocyanate (BDI), bisisocyanatocyclohexylmethane (HMDI), 2,2,4-trimethylhexamethylene diisocyanate, bisisocyanatomethylcyclohexane, bisisocyanatomethyltricyclodecane, xylene diisocyanate, tetramethylxylylene diisocyanate, norbornane diisocyanate, cyclohexane diisocyanate or diisocyanatododecane, with preference being given to hexamethylene diisocyanate (HDI), isophorone diisocyanate (IPDI), butylene diisocyanate (BDI) and bis(isoeyanatocyclohexyl)methane (HMDI). Particularly preferred are BDI, HDI, IPDI, especially preferably hexamethylene diisocyanate and isophorone diisocyanate.

Polyalkylene oxides of component A2) are preferably copolymers of ethylene oxide and propylene oxide having an ethylene oxide content, based on the total amount of oxyalkylene groups present, of 50 to 100 mol %, preferably of 60 to 85 mol %, prepared starting from polyols or amines. Suitable starters of this kind are glycerol, trimethylolpropane (TMP), sorbitol, pentaerythritol, triethanolamine, ammonia or ethylenediamine.

The polyalkylene oxides of component A2) typically possess number-average molecular weights of 1000 to 15,000 g/mol, preferably of 3000 to 8500 g/mol.

The polyalkylene oxides of component A2) further possess OH functionalities of 2 to 6, preferably of 3 to 6, more preferably of 3 to 4.

Compounds of component B) for optional use are heterocyclic, 4-ring or 6-ring oligomers of low molecular mass, aliphatic diisocyanates having a molar mass of 140 to 278 g/mol, preferably ≥168 to ≤258 g/mol, such as isocyanurates, iminooxadiazinediones or uretdiones of the aforesaid low molecular mass, aliphatic diisocyanates.

Where excess low molecular mass diisocyanate is being used, the following step is the removal of the excess of low molecular mass, aliphatic diisocyanate, preferably by thin-film distillation. Before, during and after the reaction or the distillative removal of the excess diisocyanate, it is possible for acidic or alkylating stabilizers to be added, such as benzoyl chloride, isophthaloyl chloride, methyl tosylate, chloropropionic acid, HCl or antioxidants, such as di-tertbutylcresol or tocopherol. The NCO content of the hydrophilic polyisocyanates H) is preferably 0.3 to 20 wt %, more preferably 2 to 10 wt % and very preferably 3 to 6 wt %.

In order to accelerate the formation of urea or urethane it is possible to use catalysts in component D). These are typically the compounds known to the skilled person from polyurethane technology. Preferred here are compounds from the group consisting of catalytically active metal salts which do not fall within component E), amines, amidines and guanidines. Examples include tin dibutyl dilaurate (DBTL), tin acetate, 1,8-diazabicyclo[5.4.0]undec-7-ene (DBU), 1,5-diazabicyclo[4.3.0]non-5-ene (DBN), 1,4-diazabicyclo[3.3.0]oct-4-ene (DBO), N-ethylmorpholine (NEM), triethylene-diamine (DABCO), pentamethylguanidine (PMG), tetramethylguanidine (TMG), cyclotetramethylguanidine (TMGC), n-decyltetramethylguanidine (TMGD), n-dodecyltetramethylguanidine (TMGDO), dimethylaminoethyltetramethylguanidine (TMGN), 1,1,4,4,5,5-hexamethylisobiguanidine (HMIB), phenyltetramethylguanidine (TMGP) and hexamethyleneoctamethylbiguanidine (HOBG).

Preferred is the use of amines, amidines, guanidines or mixtures thereof as catalysts of component D). Also preferred is the use of 1,8-diazabicyclo[5.4.0]undec-7-ene (DBU).

It is also possible, however, to do without catalysts of component D); this is preferred.

Employed as component E) are alkali metal salts of weak inorganic acids. By these are meant alkali metal salts of inorganic acids whose corresponding free acids in water at 25° C. have a pKa of >4.0. Examples of particularly suitable alkali metal salts of weak inorganic acids are potassium hydroxide, sodium hydroxide, potassium carbonate, sodium carbonate and sodium hydrogencarbonate, including any desired mixtures of these salts as well.

To improve the foam formation, foam stability or the properties of the resultant polyurethane foam it is possible to use compounds of component F), with such additives possibly being, in principle, all anionic, cationic, amphoteric and nonionic surfactants, and also mixtures thereof, that are known per se. Preference is given to using alkylpolyglycosides, EO/PO block copolymers, alkyl or aryl alkoxylates, siloxane alkoxylates, esters of sulphosuccinic acid, and/or alkali metal or alkaline earth metal alkanoates. Particularly preferred for use are EO/PO block copolymers. The EO/PO block copolymers are preferably used alone as component F).

Moreover, for improving certain foam properties of the resulting polyurethane foam, it is possible to use compounds of component G). These are in principle all monohydric and polyhydric alcohols that are known per se to the skilled person, and also mixtures of these alcohols. They are monohydric or polyhydric alcohols or polyols, such as ethanol, propanol, butanol, decanol, tridecanol, hexadecanol, ethylene glycol, neopentyl glycol, butanediol, hexanediol, decanediol, trimethylolpropane, glycerol, pentaerythritol, monofunctional polyether alcohols and polyester alcohols, polyether diols and polyester diols.

In the preparation of the hydrophilic polyisocyanates listed under H), which, as mentioned, are optionally employed, the ratio of the monofunctional polyalkylene oxides H2) to the low molecular mass, aliphatic diisocyanates H1) is preferably set such that for each mole of OH groups of the monofunctional polyalkylene oxides there are 1.25 to 15 mol, preferably 2 to 10 mol and more preferably 2 to 6 mol of NCO groups of the low molecular mass, aliphatic diisocyanate H1). This is followed by allophanatization and/or biurethization and/or isocyanurate formation and/or uretdione formation. Where the polyalkylene oxides H2) are bonded via urethane groups to the aliphatic diisocyanates H1), there is preferably a subsequent allophanatization. It is preferred, moreover, for isocyanurate structural units to be formed.

The reaction may take place in the presence of urethanization catalysts such as tin compounds, zinc compounds, amines, guanidines or amidines, or in the presence of allophanatization catalysts such as zinc compounds.

The reaction of the components for preparing the hydrophilic polyisocyanates listed under H) takes place typically at 25 to 140° C., preferably 60 to 100° C.

It is also possible, however, to do without catalysts in the preparation of H); this is preferred.

Examples of low molecular mass, aliphatic diisocyanates of component H1) are hexamethylene diisocyanate (HDI), isophorone diisocyanate (IPDI), butylene diisocyanate (BDI), bisisocyanatocyclohexymethane (HMDI), 2,2,4-trimethylhexamethylene diisocyanate, bisisocyanatomethylcyclohexane, bisisocyanatomethyltricyclodecane, xylene diisocyanate, tetramethylxylylene diisocyanate, norbornane diisocyanate, cyclohexane diisocyanate or diisocyanatododecane, with preference being given to hexamethylene diisocyanate (HDI), isophorone diisocyanate (IPDI), butylene diisocyanate (BDI) and bis(isocyanatocyclohexyl)methane (HMDI). Particularly preferred are BDI, HDI, IPDI, especially preferably hexamethylene diisocyanate and isophorone diisocyanate. Examples of polyisocyanates H2) of higher molecular mass are polyisocyanates having an isocyanate functionality of 2 to 6 with isocyanurate, urethane, allophanate, biuret, iminooxadiazinetrione, oxadiazinetrione and/or uretdione groups, based on the aliphatic and/or cycloaliphatic diisocyanates stated in the section above.

Preferred for use as component H1) are compounds of higher molecular mass having biuret, iminooxadiazinedione, isocyanurate and/or uretdione groups, based on hexamethylene diisocyanate, isophorone diisocyanate and/or 4,4'-diisocyanatodicyclohexylmethane. Further preferred are isocyanurates. Especially preferred are structures based on hexamethylene diisocyanate.

The monofunctional polyalkylene oxides H2) have an OH number of 15 to 250, preferably of 28 to 112, and an ethylene oxide fraction of 50 to 100 mol %, preferably of 60 to 100 mol %, based on the total amount of oxyalkylene groups present.

Monofunctional polyalkylene oxides for the purposes of the invention are compounds which have only one isocyanate-reactive group, i.e. one group which is able to react with an NCO group.

The preparation of polyalkylene oxides H2) by alkoxylation of suitable starter molecules is known from the literature (e.g. Ullmanns Enzyklopädie der technischen Chemie, 4th edition, volume 19, Verlag Chemie, Weinheim pp. 31-38). Suitable starter molecules are, in particular, saturated monoalcohols such as methanol, ethanol, n-propanol, isopropanol, n-butanol, isobutanol, sec-butanol, diethylene glycol monobutyl ether and also aromatic alcohols such as phenol or monoamines such as diethylamine. Preferred starter molecules are saturated monoalcohols of the type stated above. Particularly preferred for use are diethylene glycol monobutyl ether or n-butanol as starter molecules. The monofunctional polyalkylene oxides H2) typically possess number-average molecular weights of 220 to 3700 g/mol, preferably of 500 to 2800 g/mol.

The monofunctional polyalkylene oxides H2) preferably possess an OH group as isocyanate-reactive group.

Typically, components A) to H) are used in the following amounts (for reaction with 0.1 to 200 parts by weight of water in step (H) of the process of the invention):
- 100 parts by weight of isocyanate-functional prepolymers A)
- 0 to 30 parts by weight of heterocyclic oligomers B)
- 0 to 1 part by weight of catalysts D)
- 0 to 5 parts by weight of alkali metal salts of weak inorganic acids E)
- 0 to 10 parts by weight of surfactants F)
- 0 to 20 parts by weight of alcohols U)
- 0 to 250 parts by weight of one or more components stated under H).

Preferably components A) to H) are used in the following amounts (for reaction with 0.1 to 100 parts by weight of water):
- 100 parts by weight of isocyanate-functional prepolymers A)
- 1 to 30 parts by weight of heterocyclic oligomers B)
- 0.1 to 1 part by weight of catalysts D)
- 0 to 5 parts by weight of alkali metal salts of weak inorganic acids E)
- 0 to 5 parts by weight of surfactants F)
- 0 to 10 parts by weight of alcohols G)
- 10 to 100 parts by weight of one or more components stated under H).

More preferably components A) to H) are used in the following amounts (for reaction with 1 to 60 parts by weight of water):
- 100 parts by weight of isocyanate-functional prepolymers A)
- 5 to 15 parts by weight of heterocyclic oligomers B)
- 0 to 0.5 part by weight of catalysts D)
- 0.1 to 1 part by weight of alkali metal salts of weak inorganic acids E)
- 0 part by weight of surfactants F)
- 0 part by weight of alcohols G)
- 20 to 80 parts by weight of one or more components stated under H).

In one preferred embodiment of the process of the invention, component A1) is selected from the group consisting of hexamethylene diisocyanate, trimethylhexamethylene diisocyanate, isophorone diisocyanate, 4,4'-methylenebis(cyclohexyl isocyanate) or a mixture of at least two thereof.

In one preferred embodiment of the process of the invention, the layer has at least one of the following properties:
i. a water vapour transmissibility (MVTR) of ≤1500 g/m$^2$/24 h, preferably of 2500 g/m$^2$/24 h;
ii. a retention (determined using a weight of 6 kg over 20 seconds) of at least 25%, preferably at least 35% (g/g), based on maximum absorption to DIN EN 13726-1: 2002, Part 3.2/3.3;
iii. a thickness of at least 0.1 mm, preferably in a range from 0.1 to 50 mm, or preferably in a range from 1 to 25 mm, or preferably in a range from 1.5 to 15 mm;
iv. a density in a range from 70 to 200 preferably in a range from 80 to 170 g/l, or preferably in a range from 100 to 150 g/l.

In one preferred embodiment of the process of the invention, the first film and/or the further film constitutes a material selected from the group consisting of a thermoplastic polyurethane, a polyurethane or a mixture thereof. The material of the first and/or of the further film and/or of an optional third film preferably differs from the material of the layer in at least one property, preferably selected from the group consisting of a higher density, a lower water vapour transmissibility, a lower elongation at break, a lower thickness or a combination of at least two thereof.

In one preferred embodiment of the process of the invention, the first film and/or the further film has at least one of the following properties:
EF1 a thickness in a range from 15 to 75 μm, or preferably in a range from 20 to 50 μm, or preferably in a range from 25 to 45 μm;
EF2 a water vapour transmissibility of ≥1000 g/d m$^2$, or preferably of ≥1500 g/d m$^2$, or preferably in a range from 1000 to 20,000 g/d m$^2$, or preferably in a range from 1500 to 10,000 g/d m$^2$ (determined to DIN 13726-2:2002, Part 3.2);
EF3 an elongation at break of ≥200%, preferably ≥400%, or preferably in a range from 200 to 4000%, or preferably in a range from 500 to 3000% (determined to DIN EN ISO 527-2);
EF4 comprises apertures which make up preferably at least 3%, or preferably at least 5%, or preferably at least 10%, or are preferably in a range from 3 to 30%, or preferably in a range from 5 to 25%, or preferably in a range from 10 to 20%, based on the total area of the respective film;
FF5 is a bacterial barrier and viral barrier in accordance with ASTM F1671 (American standard), in which case the first or the further film preferably have no apertures.

The first film and/or the further film preferably have/has features FF1 and EF2, or EF2 and FF3, or EF1 and EF4, or EH1 and EH5, or EH2 and EF3, or EF2 and EF4, or FF2 and EF5, or EF3 and EF4, or EF4 and EF5, or FF3 and EF4, or EF3 and EF5, or FF4 and EF5, or EF1 and FF2 and EF3, or EF1 and EF2 and EF4, or FF1 and EF2 and EF5, or EF1 and FF3 and EF4, or EF1 and EF3 and FF5, or FF2 and EF3 and FF4, or FF2 and EF4 and EF5, or EF3 and EF4 and EF5, or FF1 and FF2 and EF3 and EF4, or EF1 and FF2 and EF3 and FF5, or EF1 and FF2 and EF4 and EF5, or EF1 and EF3 and EF4 and FF5, or FF2 and EF3 and EF4 and EF5, or FF1 and FF2 and EF3 and FF4 and EF5. Additionally preferred are films which have features combinations, with feature EF4 not occurring together with feature FF5.

In one preferred embodiment of the process of the invention, at least the first film and/or the further film has apertures which have a diameter in a range from 1 to 8 mm, preferably from 1.5 to 7 mm, or preferably from 2 to 5 mm. The apertures are preferably distributed regularly over the film in question. The film in question with apertures preferably has a number of apertures in a range from 1 to 10 apertures per cm$^2$, or preferably in a range from 2 to 8 apertures per cm$^2$, or preferably in a range from 3 to 7 per cm$^2$. The apertures may have any shape which the skilled person would select for the purpose. The apertures preferably have a circular shape. Preferably the apertures are formed by punching of the corresponding area from the first film or the further film.

The layer of the composite material produced in the process of the invention preferably comprises a polyurethane which forms from the NCO-terminated polyurethane prepolymer together with the water. It is possible in step (II) for preferably further NCO-terminated polyurethane prepolymers to be prepared synchronously or successively and to he applied synchronously or successively to the first film in step (III). Following the applying in step (III), the layer is formed from the at least one prepolymer/water mixture, and comprises at least one ply containing a polyurethane. If more than one ply of a polyurethane prepolymer/water mixture is applied to the first film, the at least two plies have either the same or different polyurethanes, in other words at least one first polyurethane and optionally at least one further polyurethane, after curing of the mixture. The at least one further polyurethane preferably has at least one different property, preferably selected from the group consisting of water vapour transmissibility, thickness, retention and density, in comparison to the first polyurethane. With preference at least one of the afore-stated properties of the first polyurethane differs from the further polyurethane by at least 10% of the respective value of the property of the first polyurethane.

After the applying in step (III), there is preferably no additional material, other than the polyurethane applied in step located between the first film and the layer. With preference, after the applying in step (III), there is no further material, apart from the polyurethane applied in step (III), between the layer and the further film. With preference, after the applying in step (III), there is no further material, apart from the polyurethane applied in step (III), located between the layer and the first film and also between the layer and the further film. In the context of the invention, the feature whereby the composite material has no additional material between the layer and the films is understood to mean that apart from the materials which are used to form the first film in I, the layer in II and the further film in III, there are no further or additional materials at all that are disposed between the first film and the layer and also between the layer and the further film and contribute preferably to the bonding of the films to the layer. It is, however, possible for further layers to be located in the interior of the composite material that contain no polyurethane. These further layers, however, do not enter into direct contact with the first or further film.

In one preferred embodiment of the process of the invention, the wound dressing has at least one of the following properties:
- WA1. a thickness in a range from 1 mm to 10 cm, preferably from 1.2 mm to 2.5 cm, or preferably in a range from 1.4 to 10 mm;
- WA2. a swelling behaviour on absorption of water of less than 200 vol %, preferably of less than 180 vol %, preferably of less than 150 vol %;
- WA3. an extent in one of the spatial directions that lies within the plane corresponding to the largest areal extent of the wound dressing of <50%, preferably of <35%, or preferably of <20%, based on the extent of the wound dressing in the third spatial direction, on contacting with a fluid;
- WA4. a combination of at least two of the properties WA1, to WA3, preferably the features WA1 and WA2, or WA1 and WA3, or WA2 and WA3, or WA1 and WA2 and WA3.

A second subject of the invention is a composite material comprising:
I. a first film comprising a first film surface and a second film surface running virtually parallel to the first film surface,
II. a layer comprising at least one first polyurethane, the layer having a first layer surface, which is in contact with the first film, and having a second layer surface which is opposite the first layer surface,
III. a further film, the further film surface of the further film being in contact with the layer via the second layer surface thereof,
wherein the composite material has no additional material between the layer and at least one of the films selected from the first film and the further film.

The dressing material preferably has no additional material between the layer and the first film. With further preference the dressing material has no additional material between the layer and the further film. With preference the dressing material has no additional material between the layer and both films. The first film and also the layer and the further film are preferably constructed from the materials, and preferably have the properties, dimensions and forms, selected from those described in each case above for these parameters in connection with the process of the invention. With preference at least one film has at least one property, dimension and/or form that is different from the layer. With further preference the layer has a different composition from the films.

The layer II preferably comprises two or more plies of the same polyurethane or of at least one further polyurethane. The at least one further polyurethane preferably has at least one different property, preferably selected from the group consisting of water vapour transmissibility, thickness, retention and density, in comparison to the first polyurethane. At least one of the afore-stated properties of the first polyurethane preferably differs from the further polyurethane by at least 10% of the respective value of the property of the first polyurethane.

In the context of the invention, the feature whereby the composite material has no additional material between the layer and the films is understood to mean that apart from the materials which are used to form the first film in I, the layer in H and the further film in III, there are no further or additional materials at all that contribute to the bonding of the films to the layer. It is, however, possible for further layers to be located in the interior of the composite material that contain no polyurethane. These further layers, however, do not enter into direct contact with the first or further film.

The direct adhesion of the layer to the films in the composite material of the invention ensures further that the layer cannot expand unhindered into all spatial directions. Instead, on contact of the layer with wound fluid, there will an expansion of the layer in the direction of the opposite film, in other words a thickening of the composite material, and there will not be any substantial widening into the areal extent direction of the composite material. By this means it is possible to prevent uncontrolled swelling of the layer into ail spatial directions.

In one preferred embodiment of the process, the layer has at least one of the following properties:
i. a water vapour transmissibility (MVTR) of $\geq 1200$ g/m$^2$/24 h, preferably of $\geq 2000$ g/m$^2$/24 h, or preferably of $\geq 2500$ g/m$^2$/24 h; (determined in a method based on DIN 13726-2:2002 Part 3.2 as described in the Methods section)
ii. a maximum absorption capacity of water of $\geq 1000\%$, or preferably of $\geq 2000\%$, or preferably of $\geq 2500\%$, based on the volume of the layer before contacting with water; (The maximum absorption of the foam was determined in accordance with DIN EN 13726-1:2002, part 3.2 on a piece of foam with a size of 5×5 cm$^2$, as described in the Methods section)
iii. a retention (determined using a weight of 6 kg over 20 seconds) of at least 25%, preferably at least 35% (g/g), based on the maximum absorption in accordance with DIN EN 13726-1:2002, part 3.2;
iv. a thickness of at least 0.1 mm, preferably in a range from 70 µm to 10 cm, or preferably in a range from 200 µm to 10 cm, or preferably in a range from 500 µm to 10 mm,
v. a density in a range from 70 to 200 g/l, preferably in a range from 80 to 170 g/l, or preferably in a range from 100 to 150 g/l.

A further subject of the invention relates to a wound dressing comprising a composite material of the invention or produced according to a process of the invention. Besides the composite material, the wound dressing preferably further comprises additional plies in the form, for example, of further films or further layer, which extend at least partly over the dimensions of the composite material. It is however, possible for materials which differ from the films and/or from the layer, intended for example to protect the composite material, to be applied to at least one side of the composite material. These are preferably materials which exhibit lower water vapour transmissibility than the layer and/or than one of the films, such as the first film or the further film. These further plies may be applied to the composite material with an adhesive.

A further subject of the invention relates to the use of a composite material of the invention or of a composite material produced according to a process of the invention in a wound dressing for improving the absorption of wound secretion and for distributing secretion in the wound dressing. Improving the absorption of wound secretion means the unhindered flow of the wound secretion into the layer, without the secretion having also to flow through further adhesives or other materials. In conventional wound dressings, the secretion is not able to reach the layer unhindered, since in those cases there are adhesives between film and layer that are able to hinder the flow of secretion. This relates in particular to commercial wound dressings which include a silicone adhesive for joining different plies within the wound dressing. The direct adhesion of the layer to the films in the composite material of the invention ensures further that the layer cannot expand unhindered into all spatial directions. Instead, on contact of the layer with wound fluid, there will an expansion of the layer in the direction of the opposite film, in other words a thickening of the composite material, and there will not be any substantial widening into the areal extent direction of the composite material. By this means it is possible to prevent uncontrolled swelling of the layer into all spatial directions.

Methods:

Unless indicated otherwise, all percentages are by weight and are based on the total amount or on the total weight of the compositions.

Unless the contrary is noted, all analytical measurements relate to measurements at temperatures of 23° C.

Determination of Tensile Stress at Break;

The tensile stress at break was determined by means of DIN EN ISO 527-2.

Thickness Measurement:

The layer thickness determination is ascertained using a compressed air gauge and attached display for delivering the layer thickness, from DR. JOHANNES HEIDENHAIN GmgH, Germany (MT25P).

Density Measurement:

For the determination of volume, a specimen is punched out using a metal punch in dimensions of 5×5 cm$^2$ (with rounded corners and a curve radius of 3 mm). The height/thickness is measured from the average of a 5-fold determination by the method described above. For subsequent calculation of the density, the mass of the specimen is determined on a Mettler Toledo XS603S balance.

Retention:

For determination of the retention, a section of foam with a size of 5×5 cm$^2$, following complete absorption, is lifted up with tweezers, allowed to drip for 30 seconds, and weighed. After that the section of foam is placed on a metal platform and weighted with a weight of 6 kg for 20 seconds. Following removal of the weight, the section of foam is weighed again and the amount of moisture that has remained is determined on a percentage basis in comparison to the maximum absorption.

Determination of MVTR (Moisture Vapour Transmission Rate)

The MVTR is determined in a method based on DIN EN13726-2:2002 (Part 3.2). A metal cylinder as described in the DIN is filled with water and closed at the top end by the film or layer under investigation. The total weight (beaker with water and film) is then determined using a balance. The measurement set-up is stored at 37° C. for 24 hours and the weight is determined again. The water loss, evaporating through the film, can be determined by subtraction. The MVTR is expressed in g/(m$^2$*24 h) or g/m$^2$/24 h.

Determination of Maximum Absorption Capacity for Water:

The maximum absorption capacity was determined in accordance with DIN EN 13726-1:2002 Part 3.2 on a flat piece of foam with a size of 5*5 cm$^2$.

EXAMPLES

Inventive Production of an Adhesive-Free Wound Contact Material (Example B 1)

125 g of Baymedix FP505 were mixed with 25 g of an aqueous solution of 1.32 wt % of sodium hydrogencarbonate, 4.8 wt % of Pluronie PE6800 and 0.4% of citric acid monohydrate with vigorous stirring for 7 seconds by means of a stirrer with an anchor stirrer blade (green 037 laboratory dissolver from Pendraulik GmbH) at 930 rpm, after which the mixture was applied to a VPT9101 PU film (Covestro Deutschland AG) by means of a knife with a 1.5 mm gap in the x-y direction. The surface of the reaction mixture that extends in the x-direction was subsequently lined with a further PU film of type VPT9101. The cover film has circular holes with a diameter of 4 mm and a spacing of 5 mm between each of the hole centre points in an arrangement in row form, with the rows being offset from one another. After a waiting time of 30 minutes at the latest, the resulting composite of the invention was suitable for use as wound contact material.

The layer in the form of the dry foam (8 mm thick) gave a maximum absorption of 1100%, a swelling of 30 vol % with an expansion of 3 mm in the x-y direction (starting from a 100 cm$^2$ measurement section in the x-y direction).

When an attempt was made to separate the composite back into its original constituents, namely the two VPT9101 PU films and the foam, the high bond strength between PU films and the foam meant that the force which had to be expended was so high that the foam suffered cohesive fracture and, consequently, foam remnants remained on the PU films.

Comparative Example (VB 1)

Production as in Example 1, except for the following:

The reaction mixture was applied to a Y 05200 release paper from Felix Schöller Group, Osnabruck, and lining took place using a type the same as the release paper, but in a needled version.

The dry foam (5 mm thick) shows a maximum absorption of 1500%, a swelling of 180 vol % and 40 mm in the x-y direction (starting from a 100 cm$^2$ measurement section in the x-y direction).

When an attempt was made to separate the composite back into its original constituents, namely the two Y 05200 release papers and the foam, the bond strength between the release papers and the foam was so low that the release paper could easily be removed without foam residues, thus equating to an adhesive fracture, without the layer being destroyed or suffering tears.

FIGURES

Figure 2:
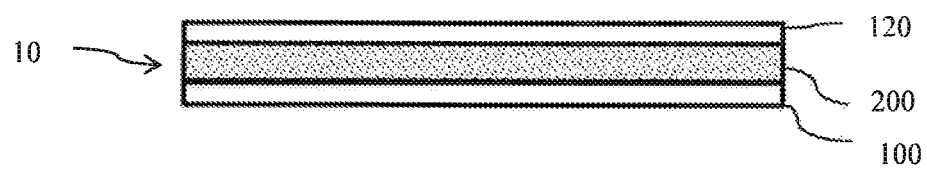
Figure 3:
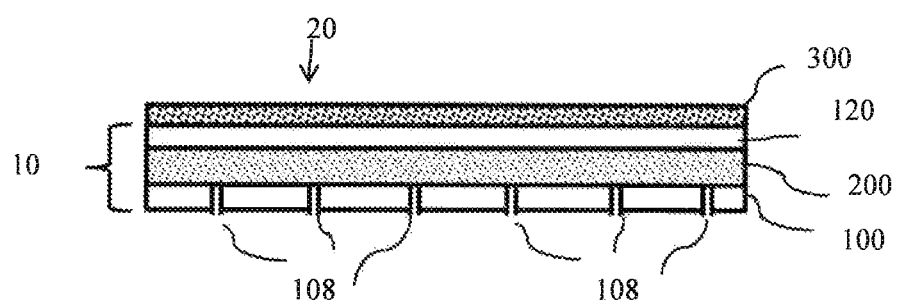

In the description of figures below, the process for producing the composite material of the invention is implemented by way of example, and the arrangement of the films and of the layer in the composite material of the invention is shown by way of example. In these figures FIG. 1: shows a schematic representation of the process of the invention with steps (I) to (IV);

FIG. 2: shows a schematic representation of a composite material of the invention;

FIG. 3: shows a schematic representation of a wound dressing.

In FIG. 1, the first film 100 is provided in step (I), corresponding to step (I) of the process of the invention. This film 100 is preferably a polyurethane film having a thickness of 20 to 50 µm. The first film 100 has a first film surface 102 and also a second film surface 104 opposite the first film surface 102, In step (II), corresponding to step (II) of the process of the invention, an NCO-terminated polyurethane prepolymer is mixed with water in a mixer 105 to give a polyurethane prepolymer/water mixture 110. The weight ratio of the NCO-terminated polyurethane prepolymer to water here is between 100:10 and 100:50, preferably 100:20. In step (III), corresponding to step (III) of the process of the invention, the mixture 110 is applied in a wet film thickness of 1500 µm using a steel knife (Film Applicator System Wasag Model 288 from ERICHISEN GmbH & Co.KG, Germany, with a knife gap height of 1.5 mm) to the first film surface 102 of the provided film 100. Within a few seconds to a few minutes, a layer 200 is formed, comprising the mixture 110, on the film 100. Before the layer 200 has undergone complete foaming, a further film 120 is applied by its farther film surface 130 to the layer 200 in step (IV), corresponding to step (IV) of the process of the invention. This preferably takes place via a roll-to-roll process directly after application of the mixture 110 to the first film 100, which is likewise provided in the form of a roll-to-roll arrangement. The film 120 is preferably already applied directly, in other words as quickly as technically possible, following application of the reaction mixture 200. In this example, the applying of the film 120 to the mixture 110 applied in step (III) occurs within a few seconds, preferably within a period of 1 to 90 seconds, or preferably within a period of 2 to 60 seconds. The composite 10 formed in step (IV) corresponds to a composite material 10 of the invention which can be further-processed into a wound dressing 20.

Represented schematically in FIG. 2 is a composite material 10 of the invention. The composite material 10 is constructed from a first film 100, which is joined via a first film surface 102 to a layer 200 via its first layer surface 202. On the second layer surface 204 of the layer 200, which is located on the first layer surface 202, the layer is joined to a further film 120. The first film 100, which in this case is designed to come into contact with the skin of the user and therefore with the wound, may preferably have apertures 108 (as shown in FIG. 3) in the first film 100, but also in the further film 120 (not shown here). Preferably, however, the only film with apertures 108 is the one designed to come into contact with the skin. The roughness of the films 100 and 120 may differ greatly on the inwardly (102, 130) and outwardly (104, 140) facing film surfaces, respectively. Moreover, the composite 10 may comprise a bacterial and/or viral barrier. This may be done either by at least one of the films 100 and/or 120 being designed as such a barrier with properties in accordance with ASTM F1671, or by the foam 200 comprising active ingredients which enable such a barrier.

FIG. 3 shows, schematically, a wound dressing 20 which comprises the composite material 10 of the invention, which has a construction as described in FIG. 2 and has been produced as described in FIG. 1. Besides the composite material 10, the wound dressing 20 optionally has an additional material 300, preferably in the form of a third film, on the film surface 104 of the further film 120 that is opposite the layer 200. This additional material 300, or the third film 300, serves primarily to protect the composite material 10 from external influences. The third film preferably protects the composite material 10 from partial tearing or being torn off when the wound dressing 20 is in use. Optionally or alternatively, the thickness of the further film 120 may also be adapted—that is, preferably, increased—in such a way that rapid tearing under high stress is prevented. Unwanted thickness of the composite material 10 may also be avoided, however, on the basis of the choice of the additional material 300. Apertures 108 in the film 100 have been made into the first film 100, which in this case comes into contact with the skin of the user and therefore with the wound.

The invention claimed is:

1. A process for producing a composite material for wound dressings, comprising the following steps:
   (I) providing a first film, having a first film surface and a second film surface running virtually parallel to the first film surface;
   (II) mixing an NCO-terminated polyurethane prepolymer with at least water to give a polyurethane prepolymer/water mixture;
   (III) applying the polyurethane prepolymer/water mixture to at least one part of the first film surface to form a layer, the layer having a first layer surface which is in contact with the first film via at least one part of the first film surface, and having a second layer surface which runs virtually parallel to the first layer surface, wherein the layer is liquid;
   (IV) covering at least one part of the second layer surface of the layer, while the layer is still liquid, with at least one part of a further film surface of a further film to give the composite material,
   wherein a bond strength between the first film and the layer and also between the layer and the further film is greater in each case than a tensile strain at break of the layer,
   wherein the composite material has no further material between the first film and the layer and also between the further film and the layer, and
   wherein the first film and/or the further film comprises a material selected from the group consisting of a thermoplastic polyurethane, a polyurethane or a mixture thereof.

2. The process according to claim 1, wherein at least steps (III) and (IV) take place within a period of less than 120 seconds.

3. The process according to claim 1, wherein the layer has a thickness after curing which is greater by 1.5 to 30 times than the thickness on application of the polyurethane prepolymer/water mixture in step (III).

4. The process according to claim 1, wherein the NCO-terminated polyurethane prepolymer has a weight fraction of low molecular mass, aliphatic diisocyanates having a molar mass of ≥140 to ≤278 g/mol of ≤1.0 wt %, based on the prepolymer, and is obtainable as component A) by reaction of
- A1) low molecular mass, aliphatic diisocyanates with a molar mass of ≥140 to ≤278 g/mol with
- A2) di- to hexa-functional polyalkylene oxides with an OH number of ≥22.5 to ≤112 mg KOH/g and an ethylene oxide fraction of ≥50 to ≤100 mol %, based on the total amount of the oxyalkylene groups present.

5. The process according to claim 4, wherein component A1) is selected from the group consisting of hexamethylene diisocyanate, trimethylhexamethylene diisocyanate, isophorone diisocyanate, 4,4'-methylenebis(cyclohexyl isocyanate) or a mixture of at least two thereof.

6. The process according to claim 1, wherein the layer has at least one of the following properties:
- i. a water vapour transmissibility (MVTR) of ≥1500 g/m²/24 h,
- ii. a retention (determined using a 6 kg weight over 20 seconds) of at least 25% (g/g), based on maximum absorption,
- iii. a thickness of at least 0.1 mm,
- iv. a density in a range from 70 to 200 g/l.

7. The process according to claim 1, wherein the first film and/or the further film have/has at least one of the following properties:
- EF1 a thickness in a range from 15 to 75 μm;
- EF2 a water vapour transmissibility of ≥1000 g/m²/24 h;
- EF3 an elongation at break of ≥200% elongation at break;
- EF4 contains apertures which make up preferably at least 3%, based on the total area of the respective film;
- EF5 exhibit a bacterial barrier and viral barrier in accordance with ASTM F1671.

8. The process according to claim 1, wherein at least the first film and/or the further film have/has apertures which have a diameter in a range from 2 to 10 mm.

9. The process according to claim 1, wherein the wound dressing has at least one of the following properties:
- WA1. a thickness in a range from 1 mm to 10 mm;
- WA2. a swelling on contacting with water of less than 200 vol %, based on a volume before contacting with water;
- WA3. an extent in one of the spatial directions that lies within the plane corresponding to the largest areal extent of the wound dressing of <50%, based on the extent of the wound dressing in the third spatial direction, on contacting with a fluid;
- WA4. a combination of at least two of the properties WA1. to WA3.

10. A wound dressing comprising the composite material produced by the process according to claim 1.

11. A method comprising utilizing the composite material produced by the process according to claim 1 in a wound dressing for improving the absorption of wound secretion and the distribution of secretion in the wound dressing.

12. The process according to claim 1, wherein in step (IV) the further film is deposited from roll to roll onto the layer, while the layer is still liquid.

* * * * *